(12) United States Patent
Kuenen et al.

(10) Patent No.: US 10,149,624 B2
(45) Date of Patent: Dec. 11, 2018

(54) METHOD AND DEVICE FOR MEASURING INTRACRANIAL PRESSURE, ICP, IN A SUBJECT

(71) Applicant: KONINKLIJKE PHILIPS N.V., Eindhoven (NL)

(72) Inventors: Maarten Kuenen, Veldhoven (NL); Ihor Kirenko, Veldhoven (NL); Koray Karakaya, Eindhoven (NL); Ronald Aarts, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 131 days.

(21) Appl. No.: 14/930,221

(22) Filed: Nov. 2, 2015

(65) Prior Publication Data

US 2016/0128587 A1    May 12, 2016

(30) Foreign Application Priority Data

Nov. 6, 2014 (EP) .................................. 14192044

(51) Int. Cl.
| | |
|---|---|
| *A61B 5/103* | (2006.01) |
| *A61B 5/117* | (2016.01) |
| *A61B 5/03* | (2006.01) |
| *A61B 3/16* | (2006.01) |
| *A61B 3/12* | (2006.01) |
| *A61B 5/00* | (2006.01) |

(Continued)

(52) U.S. Cl.
CPC ............ *A61B 5/031* (2013.01); *A61B 3/1241* (2013.01); *A61B 3/16* (2013.01); *A61B 5/0059* (2013.01); *A61B 5/0205* (2013.01); *A61B 5/02416* (2013.01); *A61B 5/1071* (2013.01); *A61B 5/11* (2013.01); *A61B 5/6814* (2013.01); *A61B 5/7278* (2013.01); *A61B 2560/0261* (2013.01); *A61B 2562/0219* (2013.01)

(58) Field of Classification Search
CPC ....................................................... A61B 5/00
USPC ................ 600/300, 301, 561, 558, 587, 595
See application file for complete search history.

(56) References Cited

U.S. PATENT DOCUMENTS

| | | | | |
|---|---|---|---|---|
| 4,893,630 | A | * | 1/1990 | Bray, Jr. ................ A61B 5/026 600/484 |
| 5,117,835 | A | * | 6/1992 | Mick ..................... A61B 5/0051 600/561 |

(Continued)

FOREIGN PATENT DOCUMENTS

| | | |
|---|---|---|
| JP | 20070301215 | 11/2007 |
| WO | 2006091811 | 8/2006 |

OTHER PUBLICATIONS

Steiner, et al., "Monitoring the injured brain: ICP and CBF", British Journal of Anaesthesia 97 (1): 26-38 (2006).

(Continued)

*Primary Examiner* — May Abouelela (57) ABSTRACT

According to an aspect, there is provided a method for measuring the intracranial pressure, ICP, in a subject, the method comprising detecting whether spontaneous retinal venous pulsations, SRVPs, are occurring in an eye of the subject as the orientation of the head of the subject changes; identifying the orientation of the head of the subject at which SRVPs start to occur or stop occurring; and using the identified orientation of the head of the subject at which SRVPs start to occur or stop occurring to determine the ICP in the subject.

15 Claims, 6 Drawing Sheets (51) Int. Cl.
*A61B 5/0205* (2006.01)
*A61B 5/11* (2006.01)
*A61B 5/024* (2006.01)
*A61B 5/107* (2006.01)

(56) References Cited

U.S. PATENT DOCUMENTS

| | | | | |
|---|---|---|---|---|
| 5,630,422 A * | 5/1997 | Zanakis | | A61B 5/0059 600/473 |
| 5,788,641 A * | 8/1998 | Policastro | | A61B 5/021 600/485 |
| 5,919,144 A * | 7/1999 | Bridger | | A61B 5/031 600/561 |
| 5,993,398 A * | 11/1999 | Alperin | | A61B 5/031 600/561 |
| 6,011,581 A * | 1/2000 | Swift | | G02B 27/0093 345/419 |
| 6,353,949 B1 * | 3/2002 | Falbo | | A61G 13/04 5/610 |
| 6,558,336 B2 * | 5/2003 | Collins | | A61B 5/031 600/301 |
| 7,117,607 B2 * | 10/2006 | Horgan | | A61B 5/1071 33/366.11 |
| 7,487,562 B2 * | 2/2009 | Frondorf | | A61G 7/005 5/600 |
| 7,562,458 B1 * | 7/2009 | Clark, Jr. | | A61G 7/018 33/333 |
| 8,512,260 B2 * | 8/2013 | Grudic | | A61B 5/021 600/300 |
| 8,571,623 B2 * | 10/2013 | Baker, Jr. | | A61B 5/14551 600/310 |
| 8,632,475 B2 * | 1/2014 | Stone | | A61B 5/031 600/559 |
| 8,821,408 B2 * | 9/2014 | Hu | | A61B 5/00 600/300 |
| 2001/0027335 A1 | 10/2001 | Meyerson et al. | | |
| 2002/0052563 A1 * | 5/2002 | Penn | | A61B 5/0215 600/561 |
| 2004/0230124 A1 | 11/2004 | Querfurth | | |
| 2005/0197579 A1 * | 9/2005 | Baker, Jr. | | A61B 5/14551 600/473 |
| 2006/0020224 A1 * | 1/2006 | Geiger | | A61B 5/031 600/561 |
| 2006/0020637 A1 | 1/2006 | Kedem | | |
| 2007/0123796 A1 | 5/2007 | Lenhardt et al. | | |
| 2007/0287899 A1 * | 12/2007 | Poupko | | A61B 5/026 600/383 |
| 2008/0058681 A1 * | 3/2008 | Casali | | A61B 3/0083 600/587 |
| 2008/0077023 A1 | 3/2008 | Campbell et al. | | |
| 2008/0081961 A1 * | 4/2008 | Westbrook | | A61B 5/0205 600/301 |
| 2009/0143656 A1 | 6/2009 | Manwaring et al. | | |
| 2010/0121213 A1 * | 5/2010 | Giftakis | | A61B 5/031 600/544 |
| 2011/0083271 A1 * | 4/2011 | Bhai | | A61G 7/015 5/610 |
| 2011/0196245 A1 * | 8/2011 | Poupko | | A61B 5/02028 600/506 |
| 2011/0201961 A1 * | 8/2011 | Hu | | A61B 5/02028 600/561 |
| 2011/0245629 A1 * | 10/2011 | Giftakis | | A61B 5/0476 600/301 |
| 2011/0298631 A1 * | 12/2011 | Tunnell | | A61G 7/05 340/689 |
| 2012/0010533 A1 * | 1/2012 | Arnett | | A61B 5/0064 600/590 |
| 2012/0136240 A1 | 5/2012 | Pranevicius et al. | | |
| 2012/0265028 A1 | 10/2012 | Hughes et al. | | |
| 2012/0310075 A1 * | 12/2012 | Russell | | A61B 5/1071 600/407 |
| 2013/0018277 A1 * | 1/2013 | Liu | | A61B 5/6803 600/561 |
| 2013/0085400 A1 * | 4/2013 | Oliveira | | A61B 5/6814 600/484 |
| 2013/0141324 A1 * | 6/2013 | Zambrano | | G06F 3/011 345/156 |
| 2013/0144185 A1 * | 6/2013 | Fuller | | A61B 3/16 600/561 |
| 2013/0267791 A1 * | 10/2013 | Halperin | | A61B 5/002 600/300 |
| 2014/0081180 A1 * | 3/2014 | Ghajar | | A61F 5/055 600/595 |
| 2014/0135597 A1 * | 5/2014 | Wolf, II | | A61B 5/0017 600/301 |
| 2014/0371545 A1 * | 12/2014 | Ben-Ari | | A61B 5/021 600/301 |
| 2014/0371634 A1 * | 12/2014 | Jin | | A61B 5/1127 600/595 |
| 2015/0272481 A1 * | 10/2015 | Glaser | | A61B 5/1116 600/301 |
| 2015/0302539 A1 * | 10/2015 | Mazar | | G08B 21/0211 705/3 |
| 2016/0066803 A1 * | 3/2016 | Hu | | A61B 5/0031 600/561 |

OTHER PUBLICATIONS

Kristiansson, et al., "Measuring Elevated Intracranial Pressure through Noninvasive Methods: A Review of the Literature", Neurosurg Anesthesiol, vol. 25, No. 4, Oct. 2013.

Raguaskas, et al., "Clinical assessment of noninvasive intracranial pressure absolute value measurement method", AAN Enterprises, Inc., Neurology 78, May 22, 2012.

Jacks, et al., "Spontaneous retinal venous pulsation: aetiology and significance", J. Neurol Neurosurg Psychiatry 2003; 74:7-9.

"Spontaneous venous pulsations should be monitored during glaucoma therapy", BR J Ophthalmol 2002; 86:1187-1196.

Golzan, et al., "Non-invasive Estimation of . Intracranial Pressure by Means of Retinal Venous Pulsatility", IFMBE 26th Southern Biomedical Engineering Conference, vol. 32, Jan. 1, 2010.

Golzan, et al., "Non-invasive Estimation of Cerebrospinal Fluid Pressure Waveforms by Means of Retinal Venous Pulsatility and Central Aortic Blood Pressure", Annals of Biomedical Engineering, Kluwer Academic Publishers—Plenum Publishers, NE, vol. 40, No. 9, Apr. 13, 2012, pp. 1940-1948.

\* cited by examiner

METHOD AND DEVICE FOR MEASURING INTRACRANIAL PRESSURE, ICP, IN A SUBJECT

CROSS-REFERENCE TO PRIOR APPLICATION

This application claims the benefit of European Patent Application No. 14192044.7, filed on Nov. 6, 2014. The application is hereby incorporated by reference herein.

TECHNICAL FIELD OF THE INVENTION

The invention relates to the measurement of intracranial pressure, ICP, in a subject, and in particular relates to a non-invasive method and device for measuring ICP.

BACKGROUND TO THE INVENTION

The intracranial pressure (ICP) of a subject is the pressure inside the human skull, and therefore, in the brain tissue. Maintenance of a stable ICP is, therefore, very important for protection of the brain. In healthy individuals, ICP typically ranges between 7 and 15 mmHg. Intracranial hypertension, i.e. ICP exceeding 20 mmHg, may lead to potentially permanent brain damage and can cause death.

Raised ICP is a common problem in neurosurgical and neurological patients and may result from any of several causes, for example a traumatic brain injury, an aneurysm, a brain tumour or stroke. Elevated ICP is a predictor of poor outcome after a traumatic brain injury.

ICP is monitored in subjects who have previously had a severe head injury, intracerebral and subarachnoid haemorrhage, edema resulting from stroke, and several other conditions. In many cases, these subjects receive therapy that has the purpose of reducing ICP or cerebral perfusion pressure (CPP), which is closely related to ICP.

Currently, the gold standard for ICP measurement involves the insertion of an intraventricular drain that is connected to an external pressure transducer, into one of the lateral ventricles. This invasive measurement has severe drawbacks, such as the need for a surgeon to insert the drain, the risk of infection (which is around 6-11% and increasing with time) and the difficulty of inserting the catheter into subjects with severe brain swelling. An alternative, yet still invasive, technique is offered by intraparenchymal probes. Although this technique is associated with a lower risk of infection, this measurement technique is hampered by a drift of the zero reference that cannot be recalibrated once the catheter is in place.

Given the strong clinical interest in ICP monitoring, a number of non-invasive techniques have been proposed to overcome the drawbacks of invasive ICP measurements:

Computed tomography can reveal anatomical changes related to elevated ICP. However, such anatomical changes do not occur in all cases of raised ICP.

Transcranial Doppler ultrasonography provides an indirect ICP assessment by measurement of the pulsatility of intracranial blood flow.

Ultrasound time-of-flight techniques measure the acoustic properties of the cranial vault or intracranial structures, assuming that these properties change due to the compression caused by elevated ICP. Only relative changes can be measured, so these techniques require baseline measurements which are often not available.

Tympanic membrane displacement measures the effect of intracranial pressure on the acoustic reflex. The technique is, however, not sufficiently accurate for clinical monitoring.

Ophthalmoscopy can detect visual changes in the eye fundus that result from impediment of venous flow, such as engorgement and papilledema. These changes are, however, late signs which are not visible during early stages of elevated ICP.

The optic nerve sheath diameter (ONSD) is another indicator of ICP and can be measured by either ultrasound or magnetic resonance imaging (MRI); however, its accuracy is hampered by the definition of the measurement location.

Ophthalmodynamometry measures the retinal venous outflow pressure, which approximately equals ICP, by applying a gradually increasing pressure on the eyeball. The ICP is measured when the retinal vein collapses as the sum of the applied external pressure and the, previously measured, intraocular pressure.

Two-depth transcranial Doppler ultrasound measures the flow properties in the ophthalmic artery both inside the cranium and outside (near the eye). Subsequently, a gradually increasing pressure is applied on the tissues surrounding the eye until the flow properties inside and outside the cranium are the same. At this point, ICP is approximated by the external pressure.

Despite a significant research effort into non-invasive ICP assessment, none of the developed methods has yet been adopted into clinical practice on a large scale. As a result, highly obtrusive invasive measurements remain the gold standard for ICP measurement. Because of the risks and drawbacks associated with the invasive procedures, ICP monitoring is simply not available in many clinical conditions.

All the ICP measurement techniques described above involve highly advanced point measurements, which can only be performed by skilled clinicians. As a result, both the invasive and the new non-invasive ICP measurements can only be performed in the hospital. This poses a significant practical issue for ICP monitoring for subjects recovering from, for example, stroke or traumatic brain injury, who may wish to stay at home. Moreover, the current techniques are far from ideal for continuously monitoring ICP.

Thus, there remains a need for a minimally intrusive and less complicated ICP measurement that would, if required, be suitable for continuous ICP monitoring outside the hospital (e.g. for use in monitoring ICP at home).

SUMMARY OF THE INVENTION

It is known in the art that pulsations occur in the eyes of subjects when the intracranial pressure (ICP) is less than the intraocular pressure (IOP). The pulsations appear in the retinal vein, which passes through both the eye (where it is subject to IOP) and the subarachnoid space (where it is subject to ICP). These pulsations are known as Spontaneous Retinal Venous Pulsations (SRVPs) and are seen as a subtle variation in the calibre of the retinal vein(s) as they cross the optic disc. SRVPs are described in "Spontaneous retinal venous pulsation: aetiology and significance" by A. Jacks and N. Miller, J Neurol Neurosurg Psychiatry, January 2003; 74(1): 7-9. These pulsations are a common phenomenon in healthy individuals and tend to disappear in people whose ICP is elevated. Although the exact physiological reasons for the absence of venous pulsations in case of elevated ICP are still unclear, the appearance of SRVPs in a subject's eye is determined by the balance between ICP and IOP. In particular, SRVPs appear or disappear when IOP equals ICP (i.e. SRVPs occur in the eye when ICP is less than IOP, and SRVPs are absent when ICP is greater than IOP).

As the head of the subject is tilted from a normal upright position, the change in height of the intracranial space (which is at the ICP) relative to the eye (which is at the IOP) introduces a hydrostatic pressure difference. At a certain tilt angle, the hydrostatic pressure difference can lead to the IOP equaling the ICP, which can be determined by observing the angle at which SRVPs appear or disappear. Thus, the invention provides that the presence of SRVPs are detected in a subject's eye as the angle of the subject's head changes, and the angle at which the SRVPs appear or disappear (as appropriate depending on the direction in which the head is being tilted) is used to determine the ICP.

According to a first aspect, there is provided a method for measuring the intracranial pressure, ICP, in a subject, the method comprising detecting whether spontaneous retinal venous pulsations, SRVPs, are occurring in an eye of the subject as the orientation of the head of the subject changes; identifying the orientation of the head of the subject at which SRVPs start to occur or stop occurring; and using the identified orientation of the head of the subject at which SRVPs start to occur or stop occurring to determine the ICP in the subject.

In some embodiments the step of using the identified orientation to determine the ICP in the subject comprises determining a pressure difference between the intraocular pressure, IOP, in the eye of the subject and the ICP at a predetermined orientation using the identified orientation.

In some embodiments the step of using the identified orientation to determine the ICP in the subject further comprises determining the ICP from a measurement of the IOP in the eye of the subject at the predetermined orientation and the determined pressure difference at the predetermined orientation.

In some embodiments the predetermined orientation is the orientation where the head of the subject is upright.

In some embodiments, in the event that no orientation is identified at which SRVPs start to occur or stop occurring, the method further comprises the step of providing an output indicating that the ICP is beyond a threshold value.

In some embodiments the orientation of the head of the subject is the angle of rotation of the head about an axis that is perpendicular to a sagittal plane through the head or body of the subject.

In some embodiments the orientation is measured using a sensor that is arranged to move with the head of the subject.

In some embodiments the sensor is part of a device that is being worn on the head of the subject.

In alternative embodiments the orientation is measured using a sensor that is attached to or otherwise part of a table, bed or chair on which the subject is sitting or lying, and wherein the method further comprises the step of changing the orientation of the table, bed or chair to change the orientation of the head of the subject while detecting whether SRVPs are occurring in the eye of the subject.

In some embodiments the sensor is an accelerometer or a gyroscope.

According to a second aspect there is provided a computer program product comprising a computer readable medium having computer readable code embodied therein, the computer readable code being configured such that, on execution by a suitable computer, processor or control unit, the computer, processor or control unit is caused to perform any of the methods described above.

According to a third aspect there is provided a device for measuring the intracranial pressure, ICP, in a subject, the device comprising a first sensor for detecting whether spontaneous retinal venous pulsations, SRVPs, are occurring in the eye of the subject as the orientation of the head of the subject changes; a second sensor for measuring the orientation of the head of the subject; and a control unit configured to identify the orientation of the head of the subject at which SRVPs start to occur or stop occurring from outputs from the first sensor and second sensor; and use the identified orientation of the head of the subject at which SRVPs start to occur or stop occurring to determine the ICP in the subject.

In some embodiments the control unit is configured to use the identified orientation to determine the ICP in the subject by determining a pressure difference between the intraocular pressure, IOP, in the eye of the subject and the ICP at a predetermined orientation using the identified orientation.

In some embodiments the control unit is configured to use the identified orientation to determine the ICP in the subject by determining the ICP from a measurement of the IOP in the eye of the subject at the predetermined orientation and the determined pressure difference at the predetermined orientation.

In some embodiments the device further comprises a sensor or measuring apparatus for measuring the IOP of the subject.

In some embodiments, the predetermined orientation is the orientation where the head of the subject is upright.

In some embodiments, the control unit is further configured to provide an output indicating that the ICP is beyond a threshold value in the event that no orientation is identified at which SRVPs start to occur or stop occurring.

In some embodiments the orientation of the head of the subject is the angle of rotation of the head about an axis that is perpendicular to a sagittal plane through the head or body of the subject.

In some embodiments the device is configured to be worn on the head of the subject.

In alternative embodiments the second sensor is attached to or otherwise part of a table, bed or chair on which the subject is to sit or lie, wherein the table, bed or chair is adapted so that the orientation of the table, bed or chair can be changed in order to change the orientation of the head of the subject.

In some embodiments the second sensor is an accelerometer, a gyroscope or a camera.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

As noted above, the invention provides that intracranial pressure (ICP) is determined by applying a variable hydrostatic pressure difference between ICP and intraocular pressure (IOP) by tilting the head, which allows the pressure of spontaneous retinal venous pulsation (SRVP) onset or cessation to be found. The angle at which SRVP onset or cessation occurs is then used to determine the ICP. Thus, ICP can be found in an unobtrusive fashion, and can be measured, for example, using a simple user-worn or carried device, such as a pair of spectacles, an eye patch, a headset, a helmet, etc.

Figure 1:
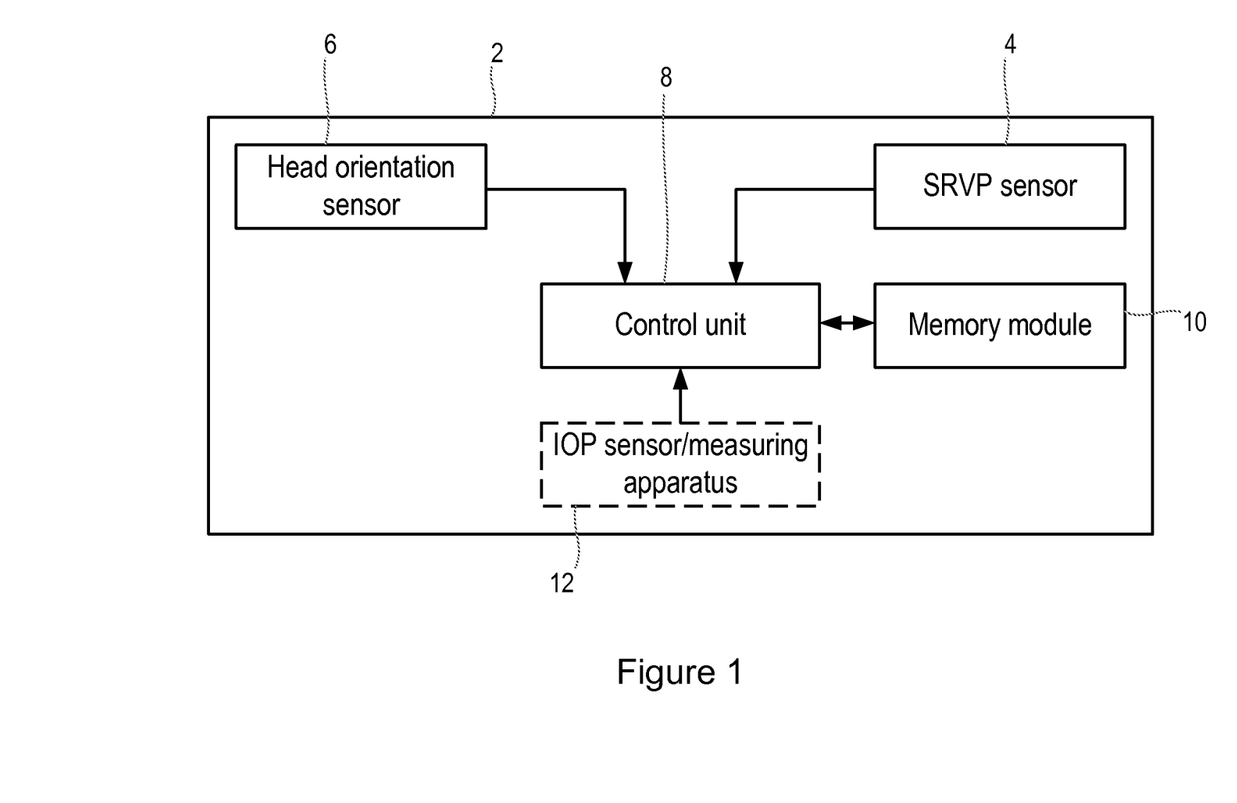
FIG. 1 is a block diagram of a device for measuring ICP according to an embodiment of the invention.

FIG. 1 shows a block diagram of a device for measuring ICP according to an embodiment of the invention. The device 2 comprises a sensor 4 for measuring or detecting the presence of SRVPs in an eye of a subject and a sensor 6 for measuring the height of the intraocular space relative to the intracranial space in the subject (or the difference in height between the intraocular space and the intracranial space). This height difference can be measured by a sensor 6 that measures or estimates the orientation of the subject's head. In preferred embodiments, the sensor 6 is for detecting or measuring the angle of the head of the subject relative to a reference position. In other embodiments, the sensor 6 can comprise a camera that observes the head of the subject (in which case the images from the camera are processed to identify the orientation of the head and thus the difference in height between the intraocular space and the intracranial space).

The sensors 4, 6 provide respective measurements (in the form of appropriate signals) to a control unit 8 that processes the measurements to determine the ICP of the subject. The control unit 8 controls the operation of the device 2 according to the invention. The control unit 8 can comprise one or more processors, processing units, multi-core processors or processing modules.

The device 2 further comprises a memory module 10 for storing computer readable program code that can be executed by the control unit 8 to perform the method according to the invention. The memory module 10 can also be used to store the measurements from the sensors 4, 6 before, during and after processing by the control unit 8, and any intermediate products or other data required to complete the processing.

The sensor 4 can be any suitable sensor for measuring or detecting the presence of SRVPs in an eye of a subject, and the output of the sensor 4 may, in some cases, be a signal that simply indicates that SRVPs are present or absent. In some embodiments, as part of detecting the presence of SRVPs, the sensor 4 should be able to distinguish arterial pulsations from venous pulsations.

One suitable class of sensors use optical sensor technologies similar to those found in pulse oximetry (SpO2) sensors. SpO2 sensors measure pulsatile blood flow by detecting pulsatile changes in light absorption spectra at specific wavelengths, as it is well-known that oxygenated blood has a different light absorption spectrum than deoxygenated blood. By measurement of the absorption spectrum at two distinct wavelengths (for example at red (e.g. 660 nm) and infrared (e.g. 940 nm) wavelengths), the output from an SpO2 sensor can be used to calculate the relative amount of oxygenated and deoxygenated blood, and, therefore, the percentage of blood that is oxygenated in arteries (since veins typically do not pulsate).

For detecting the presence of SRVPs in an eye of the subject, a sensor 4 can be used that is based on reflective pulse oximetry and that includes one or more light sources that output light at two or more distinct wavelengths and one or more light sensors that can measure light at those two or more distinct wavelengths. The light is shone into the subject's eye (at an intensity that will not damage the eye) and the intensity of the reflected light at each wavelength is measured by the light sensor(s). From the signals representing the intensity of the reflected light a baseline signal, an arterial pulsation signal, and a venous pulsation signal can be determined. It will be appreciated that in some embodiments the sensor 4 can include the appropriate processing circuitry for determining the presence or absence of SRVPs from the light signals, but in other embodiments the sensor 4 can output the raw light intensity signals to the control unit 8, and the control unit 8 can process the light intensity signal to determine the presence or absence of SRVPs.

In some embodiments, the sensor 4 can comprise a sensor for measuring the SpO2 in the eye and another pulse oximetry sensor that is used to measure the SpO2 at the subject's finger (or other suitable location), and the SpO2 measurements are compared. When SRVPs are present, they will contribute to the pulsatile signal measured in the eye, and will cause a lower SpO2 reading in the eye than in the finger since SRVPs constitute deoxygenated pulsations. On the other hand, when SRVPs are absent, only the eye artery will contribute to the SpO2 reading, which will, therefore, be the same as the reading from the finger sensor.

In some embodiments, the measurement of the SpO2 at the finger is used for calibration purposes. The SpO2 measurement at the finger (or any other location where the SpO2 reading reflects the arterial oxygen saturation) provides a value for $SpO2_{artery}$ (as in equation (1) below). If no SRVPs are present, the SpO2 reading in the eye will be the same as the reference measurement; if SRVPs are present, the SpO2 reading in the eye will be below the reference measurement. An example of this relationship is shown in FIG. 3(c) below, where $SpO2_{artery}=98\%$.

In other embodiments, the sensor 4 can just comprise a sensor for measuring the SpO2 in the eye, and the onset or cessation of SRVPs is detected by detecting a significant change in the SpO2 reading. In particular, the onset of SRVPs is detected by detecting a change in the SpO2 reading from a constant value as the head orientation changes, and the cessation of SRVPs is detected by detecting that the SpO2 reading is now a constant value whereas previously it was changing as the head orientation changes.

As described by Golzan et al in "Non-invasive estimation of cerebrospinal fluid pressure waveforms by means of retinal venous pulsatility and central aortic blood pressure," Ann. Biomed. Eng, 40 (9), pp. 1940-1948, 2012, the amplitude of SRVPs depends approximately linearly on the difference between IOP and ICP. In embodiments of the invention, the SRVP amplitude $A_{vein}$ is considered as a measure for venous pulsatility. The SpO2 reading is then calculated as the weighted average of SpO2 in pulsatile arterial and venous blood, as $$SpO2_{eye} = \frac{A_{artery}SpO2_{artery} + A_{vein}SpO2_{vein}}{A_{artery} + A_{vein}} \quad (1)$$

Figure 3:
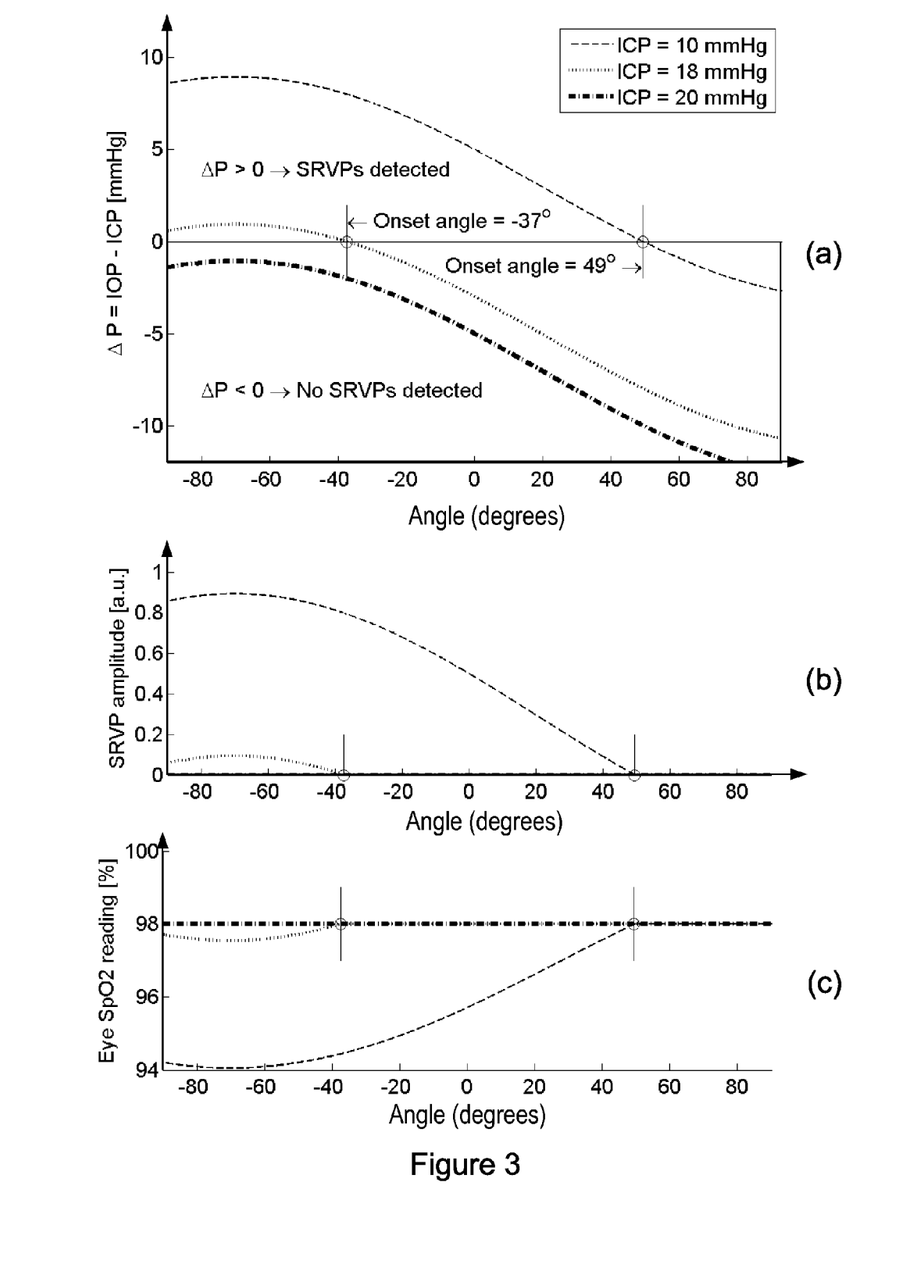
FIG. 3 shows a plot illustrating the relationship between the angle of the subject's head and the difference between IOP and ICP for three values of ICP, a plot illustrating the relationship between the angle of the subject's head and the SRVP amplitude for the three values of ICP, and a plot illustrating the relationship between the angle of the subject's head and the SpO2 measurement in the subject's eye for the three values of ICP.

In this calculation, the amplitude $A_{artery}$ of arterial pulsation and SpO2 of both arterial (here 98%) and venous blood are assumed constant. The amplitude of venous pulsation is the only parameter that changes as a function of angle, and, therefore, the SpO2 reading will reflect venous pulsation as indicated in FIG. 3. As can be observed in FIG. 3, the onset of SRVPs corresponds to the angle at which the SpO2 reading from the eye reaches a constant value that reflects the arterial oxygenation $SpO2_{artery}$.

In another embodiment, the presence or absence of SRVPs can be detected by exploiting the fact that venous pulsations occur during diastole, whereas arterial pulsations occur during systole. This means that there is an approximately 180 degree phase difference between the arterial and venous pulsatile signals. In one approach, the arterial and venous pulsation signals may be added together, and the sum of the signals would be characterised by a dominant frequency that is exactly twice the heart rate since peaks in the venous signal coincide with troughs in the arterial signal, thus creating two distinct peaks during each heartbeat. In case a single peak is observed in the summed signal per heartbeat, this peak must relate to the arterial pulse and hence there are no SRVPs. If two peaks are observed per heartbeat, one will correspond to the arterial pulse and one will correspond to the SRVPs.

Another type of sensor 4 that can be used to detect the presence or absence of SRVPs is a fundus camera along with video processing software that can automatically see the veins pulsating (for example as described e.g. by Moret et al in "Visualization of fundus vessel pulsation using principal component analysis," IOVS, 52(8), pp. 5457-5464, 2011).

As noted above, in preferred embodiments sensor 6 is for detecting or measuring the orientation (e.g. angle) of the head of the subject and can be any suitable sensor whose output can be used to provide an indication of the height of a subject's eye(s) or intraocular space relative to their intracranial space. The angle of the head of the subject (also referred to as a tilt angle) is the angle of rotation of the head around an axis that is perpendicular to a sagittal plane through the subject's head or body (where sagittal plane is given its usual meaning within anatomy). The angle can be measured from any suitable reference point, such as a vertical axis (e.g. parallel to the direction in which gravity acts) or a horizontal plane (where vertical and horizontal are defined in the Earth's reference frame). Suitable sensors for measuring the orientation include a gyroscope, an accelerometer or a camera that observes the subject's head.

Figure 2:
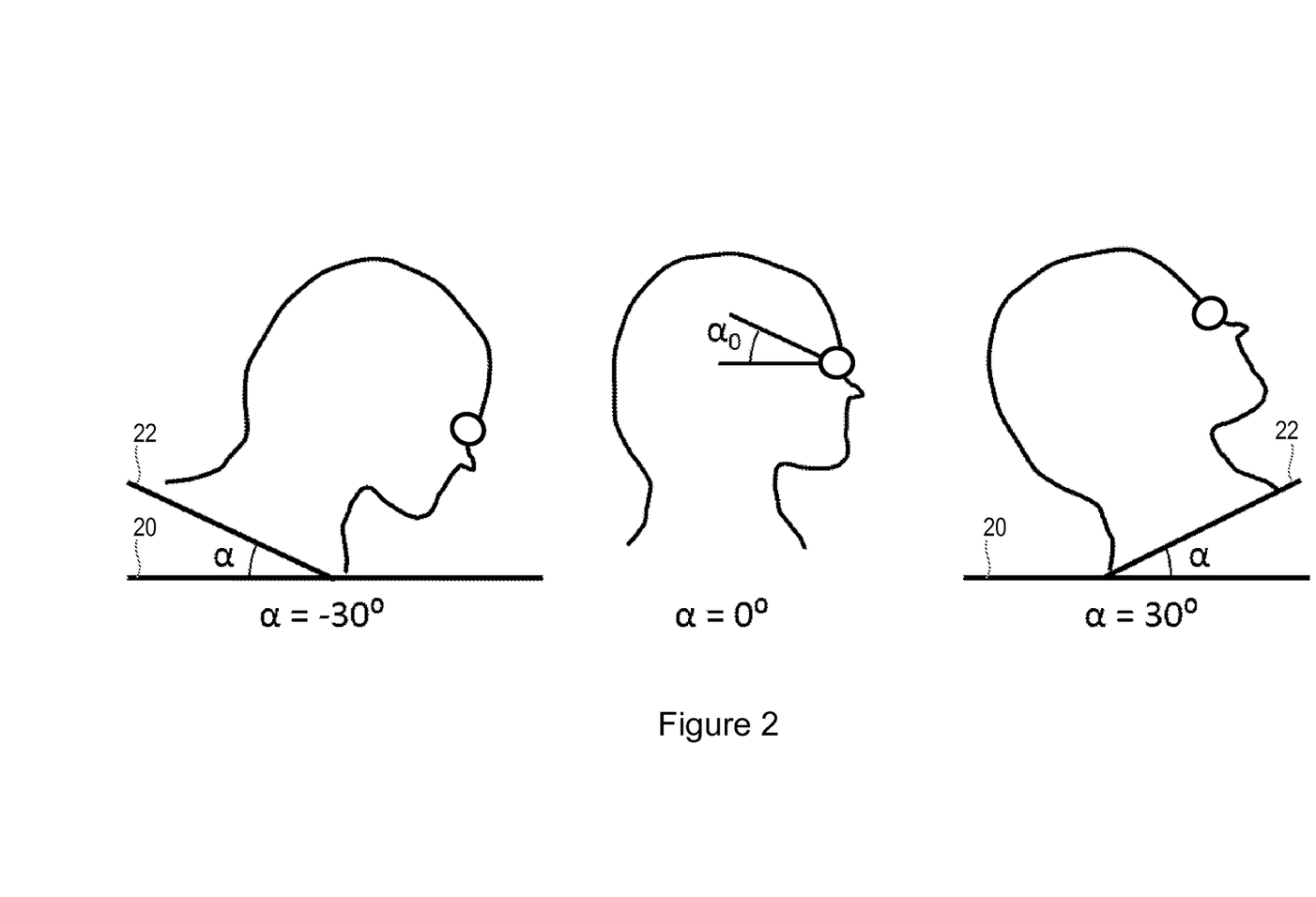
FIG. 2 illustrates possible tilt angles of the subject's head.
Figure 6:
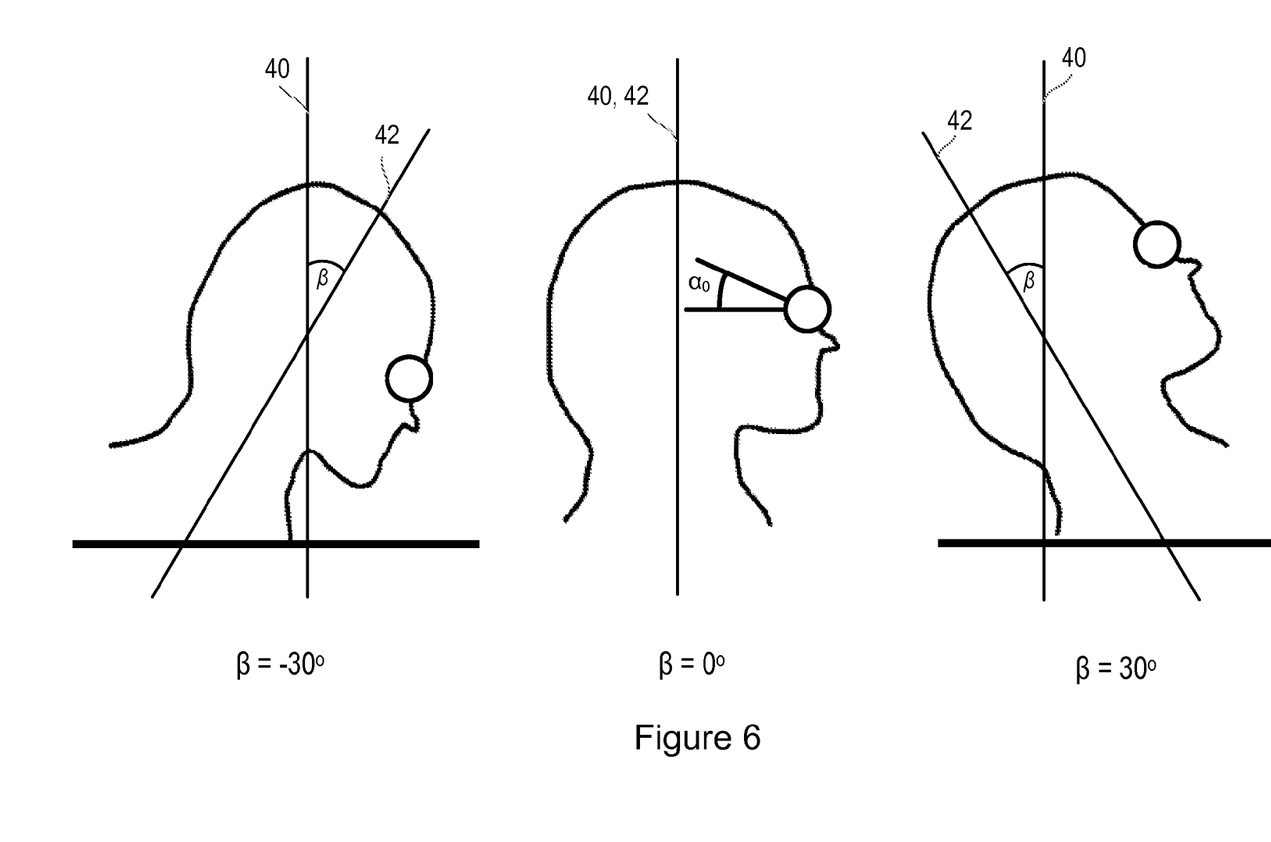
FIG. 6 shows an alternative angle representing the tilt angle of the head that can be measured.

FIG. 2 illustrates an exemplary angle α that can be measured by the sensor 6 and that can represent the tilt angle of the subject's head. In this example, the angle α is measured between a plane 20 that lies perpendicular to the vertical direction in the Earth's reference frame (plane 20 is also referred to as a horizontal plane 20) and a transverse plane 22 that passes through the subject's head (with the transverse plane being given the usual meaning in anatomy) and represents the rotation of the subject's head about an axis that is perpendicular to a sagittal plane through the subject's body (although it will be appreciated that the axis of rotation does not need to pass through the subject's head or body as shown in FIG. 2). FIG. 2 illustrates a subject's head at three different angles with respect to the horizontal plane 20, with α=−30°, α=0° and α=30°. When α=0° the subject's head is referred to as being 'upright', and in this illustration, negative angles represent the subject's head tilting forward from the upright position and positive angles represent the subject's head tilting backwards from the upright position. As noted above, the angle of rotation can alternatively be measured with respect to a vertical axis (as shown in FIG. 6 below), or any other desired reference axis.

It will be appreciated that the angle of the subject's head can change with respect to the Earth reference frame by the subject moving their head relative to the rest of their body (i.e. by flexion or extension of the neck), or by the upper part or the whole body of the subject being tilted. In particular, in some embodiments, a subject can sit or lie on a table, bed or chair that can be manually or automatically moved through a range of angles to tilt the subject and enable ICP to be measured. In these embodiments, the sensor 6 can be integrated with the table, bed, chair or tilting mechanism, or be part of a device that is worn or carried by the subject while the subject sits or lies on the table, bed or chair. In these embodiments, it will be appreciated that the tilt angle of the subject's head will be the same as the tilt angle of the table, bed or chair.

In some embodiments, the orientation sensor 6 is a gyroscope that is held in a fixed relationship relative to the subject's head when the device 2 is in use (e.g. by being incorporated into a pair of glasses or being part of a tilt table or bed) so that a change in angle of the subject's head (and the angle relative to a plane that is fixed in the Earth's reference frame) can be determined from the output of the gyroscope.

Another suitable type of angle sensor 6 is an accelerometer that is held in a fixed relationship relative to the subject's head when the device 2 is in use. When there is little or no motion (or rather, acceleration) of the subject's head, the output of the accelerometer will represent the direction in which gravity acts, and it is possible to determine the angle of the subject's head relative to a plane that is fixed in the Earth's reference frame from the accelerometer measurement. The accelerometer 6 may be a one-, two- or three-dimensional accelerometer that measures accelerations in one-, two- or three dimensions. The accelerometer 6 can operate according to any desired operating or sampling frequency to measure the acceleration, for example 50 Hz.

As noted above, the sensor 6 is provided in order to measure the height of the intraocular space relative to the intracranial space in the subject. Since the intraocular space and intracranial space are not necessarily at the same height when the head is in an upright position (depending on the anatomy of the subject), it is necessary to account for this initial height difference in order to be able to calculate the relative height of the intraocular space and the intracranial space. This initial height difference can be determined by measuring or observing the angle $α_0$ between a plane passing through the centre of the intraocular space and the centre of the intracranial space and a horizontal plane. $α_0$ is shown in FIG. 2.

The height difference between the intraocular space and the intracranial space can be calculated using:

$$\Delta h = L \sin(\alpha - \alpha_0) \quad (2)$$

where L is the distance between the intraocular space and the intracranial space (which is determined by the anatomy of the subject).

In some embodiments, L and/or $α_0$ can be measured through observation of the subject, but in other embodiments the values for L and/or $α_0$ can be fixed values (e.g. 6 cm for L and 25° for $α_0$) or a value determined from population-based statistics.

In some embodiments of the invention, the device 2 additionally comprises a sensor or measuring apparatus 12 for measuring the IOP of the subject. This sensor 12 is used to measure the IOP of the subject and to provide the IOP measurement to the control unit 8 for use in determining the ICP of the subject according to the invention. In embodiments where the device 2 does not include the sensor 12, the control unit 8 can be configured to obtain an IOP measurement from an external source, such as a separate IOP measurement apparatus or a computer that has a suitable IOP measurement stored therein, or an IOP measurement can be manually input into the device 2 by a user of the device 2 (e.g. by the subject themselves or by a healthcare provider). The IOP measurement apparatus (whether part of or separate from the device 2), can be a Goldmann tonometer or, more preferably (in view of the aim to make the measurement of ICP as unobtrusive and non-invasive as possible), a tonometer that does not require physical contact with the eye, such as tonometers that use puffs or pulses of air to measure the IOP. In some embodiments, the IOP can be measured using a contact lens placed on the subject's eye. Suitable contact lenses include the Sensimed Triggerfish® (www.sensimed.ch/en/sensimed-triggerfish/sensimed-triggerfish.html).

In the embodiment of the invention illustrated in FIG. 1, the device 2 comprises a single unit that collects and processes the measurements of SRVP and the orientation of the head. This device 2 can be worn or carried by the subject (and can be, for example, a pair of spectacles, an eye patch, a headset, a helmet, etc.), or it can be integrated into another apparatus, such as a bed, chair or table. In alternative embodiments, the processing of the measurements can be performed in a control unit that is remote from the sensors 4, 6 (for example in a unit that is worn on a different part of the body of the subject, in a base unit or a computer that can be located in the subject's home, or a remote server located in the premises of a healthcare service provider), in which case the device 2 will comprise a sensor unit to be worn by the subject (that is similar to that shown in FIG. 1) and that comprises suitable transmitter, transceiver or communication circuitry for transmitting the measurements to a control unit in the remote unit. In either embodiment, the device 2 can be part of an ICP monitoring system which comprises a display or other visual indicator (that can themselves be part of or separate from the device 2) that can be used to indicate the determined ICP to the subject or a clinician.

In practical implementations, the device 2 may comprise other or further components to those shown in FIG. 1 and described above, such as a user interface that allows the subject to activate and/or operate the device 2, and a power supply, such as a battery, for powering the device 2. The user interface may comprise one or more components that allow a user (e.g. the subject) to interact and control the device 2. As an example, the one or more user interface components could comprise a switch, a button or other control means for activating and deactivating the device 2 and/or measurement process. The user interface components can also or alternatively comprise a display or other visual indicator for providing information to the subject about the operation of the device 2, including displaying the measured ICP.

FIG. 3 shows several plots illustrating how head orientation or angle is related to the difference between IOP and ICP (FIG. 3(*a*)), the amplitude of SRVPs in the subject's eye (FIG. 3(*b*)) and the SpO2 reading in the subject's eye (FIG. 3(*c*)) for three different values of ICP. For the plots in FIG. 3, the IOP is assumed to be 15 mmHg, the value of K (see below) is 6 mmHG and $\alpha_0$ is assumed to be 20°. The angle shown on the x-axes is $\alpha$.

FIG. 3(*a*) illustrates the relationship between the angle $\alpha$ of the subject's head and the difference between IOP and ICP ($\Delta$P) for three different values of ICP: ICP=10 mmHg (represented by the dashed line), 18 mmHg (represented by the dotted line) and 20 mmHg (represented by the dot-dash line). When $\Delta$P is greater than 0 (i.e. IOP is greater than ICP), SRVPs will be present in the subject's eye as shown by FIG. 3(*b*) (and detectable by sensor 4 as shown in FIG. 3(*c*)). When $\Delta$P is less than 0 (i.e. IOP is less than ICP), SRVPs will not be present in the subject's eye (and thus no SRVPs will be detected by sensor 4).

Based on an IOP of 15 mmHg, with an ICP of 10 mmHg, the angle $\alpha$ at which the SRVPs appear (the 'onset angle', which is denoted $\alpha_{SRVP}$) is 49°. At angles less than 49°, SRVPs are present (as shown by a non-zero SRVP amplitude in FIG. 3(*b*)) and detectable through observing the SpO2 measurement of the eye (as shown in FIG. 3(*c*). At angles greater than 49°, SRVPs are not present (indicated by the zero amplitude in FIG. 3(*b*) and the eye SpO2 measurement reaching a maximum value (98%).

In the second example where ICP is 18 mmHg, the angle $\alpha$ at which the SRVPs appear (the 'onset angle', $\alpha_{SRVP}$) is −37°. At angles less than −37°, SRVPs are present, and at angles greater than −37°, SRVPs are not present.

In the third example where ICP is 20 mmHg, the ICP is too high relative to the IOP for the hydrostatic pressure change caused by tilting the head to allow SRVPs to appear. Thus, there is no angle $\alpha$ at which the SRVPs appear.

Figure 4:
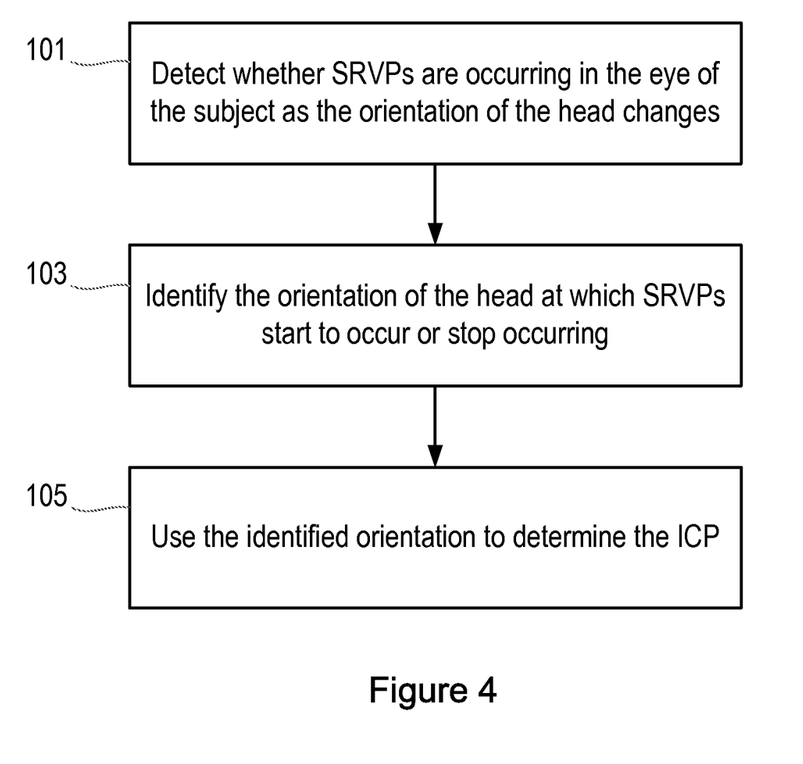
FIG. 4 is a flow chart illustrating a method of measuring ICP according to an embodiment of the invention.

FIG. 4 is a flow chart illustrating a method of measuring ICP according to an embodiment of the invention. In a first step, step 101, the SRVP sensor 4 is used to detect whether SRVPs are occurring in the eye of the subject. The SRVP sensor 4 is used to detect the presence of SRVPs as the orientation of the subject's head changes (with the orientation changing due to rotation of the head about an axis that is perpendicular to a sagittal plane through the subject's body). It will be appreciated that the subject may start the method with their head at any possible angle (for example 0°, −90°, −90°, or any angle in between or beyond).

As the orientation of the subject's head changes, the SRVP sensor 4 may detect at a certain point or time that SRVPs are no longer present (or that SRVPs are now present whereas previously they were not, depending on the direction of rotation of the subject's head). In step 103, the orientation of the subject's head at which the SRVP sensor 4 detects that SRVPs are no longer present (or that SRVPs are now present whereas previously they were not) is determined by the orientation sensor 6.

It will be appreciated that steps 101 and 103 can be performed in several ways. In one implementation, both the SRVP sensor 4 and orientation sensor 6 continuously (or periodically according to their measuring frequency) measure their respective characteristics (i.e. presence of SRVP and orientation of the head), and these measurements can be processed in real-time or at a later time to identify when the SRVPs appeared/disappeared (as appropriate) and the orientation of the head at that time. In an alternative implementation, the output of the SRVP sensor 4 can be processed in real-time to identify when the SRVPs appear/disappear and the orientation sensor 6 activated when that occurs to measure the orientation of the head.

Once the orientation at which the SRVPs appear or disappear (depending on the direction of rotation of the head) is determined, the method moves to step 105 in which the identified orientation is used to determine the ICP. In the following, the orientation/angle at which the SRVPs appear or disappear is denoted $\alpha_{SRVP}$. An exemplary technique for determining the ICP using the angle $\alpha_{SRVP}$ is described below with reference to FIG. 5 which is a schematic diagram illustrating the processing steps according to an embodiment of the invention. Processing block 30 corresponds to step 103 in FIG. 4.

Figure 5:
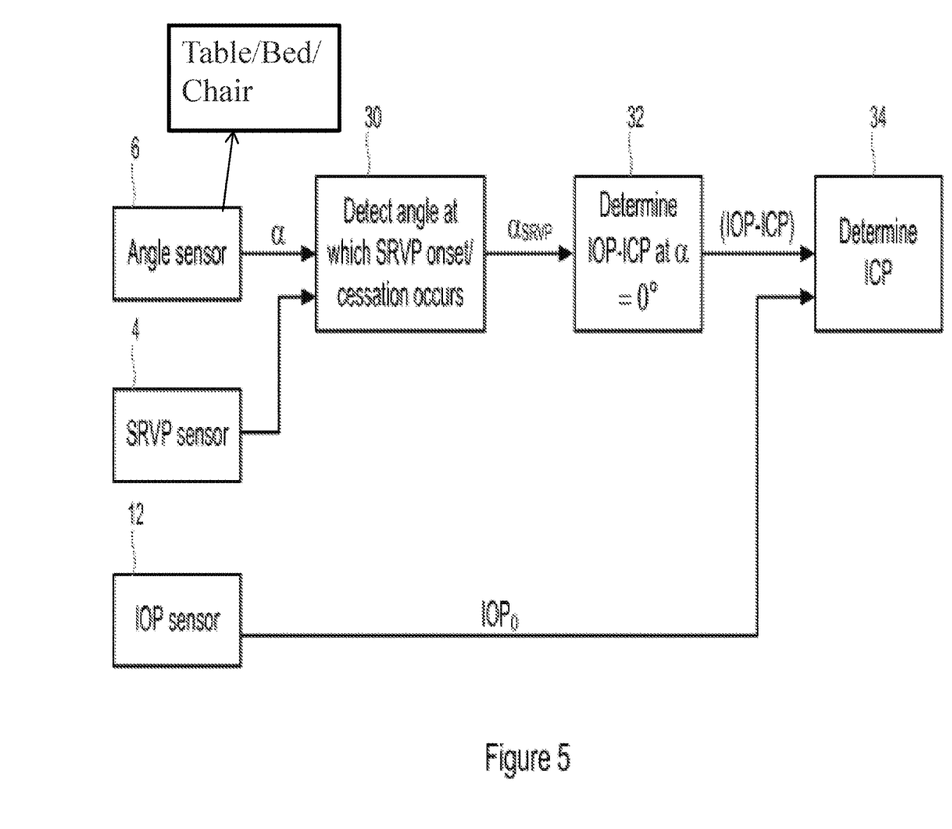
FIG. 5 is a schematic diagram illustrating the processing steps according to an embodiment of the invention.

As noted above, changing the tilt angle of the subject's head influences the hydrostatic pressure difference between ICP and IOP. The change in the hydrostatic pressure may mean that at a certain angle of the subject's head IOP will equal ICP, which will be indicated by the angle $\alpha_{SRVP}$ at which SRVPs in the subject's eye appear or disappear. Thus, at $\alpha_{SRVP}$, IOP=ICP.

The nominal pressure difference between IOP and ICP, i.e. the pressure difference when the head is upright (the angle $\alpha$ is 0°), which is denoted $\Delta P_0$, can be directly determined as a function of the angle $\alpha_{SRVP}$.

The pressure difference between IOP and ICP at angle $\alpha$ is given by:

$$\text{IOP-ICP} \approx K[\sin(\alpha-\alpha_0)+\sin(\alpha_0)]+\Delta P_0 \quad (3)$$

where K is determined only by the anatomy of the head of the subject. $K \sin(\alpha_{SRVP})$ represents the hydrostatic pressure difference between the intracranial and intraocular spaces. This is determined only by the difference in height between the two spaces (given by equation (2) above), and K is the amplitude of the pressure difference and is determined by the distance between the centres of the two spaces (L), multiplied by a hydrostatic pressure per unit of distance (which is given by $\rho g$, where $\rho$ represents density of the medium, e.g., equal to that of water, 1000 kg/m$^3$, and g represents the gravitational acceleration, e.g. 9.81 m/s$^2$). The value of K depends only on the anatomy of the subject (and can be a value derived from a statistical analysis of a suitable population of subjects).

At angle $\alpha_{SRVP}$, the pressure difference is 0, so $\Delta P_0$ can be calculated in processing block 32 from:

$$\Delta P_0 = -K[\sin(\alpha_{SRVP}-\alpha_0)+\sin(\alpha_0)] \quad (4)$$

Once $\Delta P_0$ has been derived, the ICP of the subject can be determined (processing block 34). This requires a nominal measurement of the IOP of the subject, i.e. a measurement of IOP when the head is in the nominal position (i.e. where the angle $\alpha$ is 0°). This measurement is denoted ION and is provided by IOP sensor 12. Preferably the measurement IOP$_0$ is obtained around the time that the ICP is determined since IOP can vary by around 3-6 mmHg through the day. As noted above, the IOP sensor 12 can be based on Goldmann tonometry, a sensor built-in to a contact lens or other available techniques.

Using the IOP measurement, the ICP is determined in block 34 from:

$$\text{ICP}=\text{IOP}-\Delta P_0 \quad (5)$$

Another way of viewing the calculation of $\Delta P_0$ described above is to split it into two stages. In the first stage or step, the height difference between the intraocular space and the intracranial space is determined from the angle $\alpha_{SRVP}$ using equation (2) above. The hydrostatic pressure difference $\Delta P_0$ is then determined from the height difference at $\alpha_{SRVP}$ using the standard equation for hydrostatic pressure:

$$\Delta P_0 = \rho g \Delta h \quad (6)$$

(such that $K=L\rho g$). Both $\rho$ and g are known constants, representing density of the medium (e.g., equal to that of water, 1000 kg/m$^3$), and the gravitational acceleration (on Earth, 9.81 m/s$^2$).

As noted above FIG. 2 illustrates one possible way of measuring the angle of the head. An alternative way of measuring the angle of the head is shown in FIG. 6. FIG. 6 illustrates an exemplary angle $\beta$ that can be measured by the sensor 6 and that can represent the tilt angle of the subject's head. In this example, the angle $\beta$ is measured between a vertical axis 40 that is parallel to the vertical direction in the Earth's reference frame and a coronal plane 42 that passes through the subject's head (with the coronal plane being given the usual meaning in anatomy) and represents the rotation of the subject's head about an axis that is perpendicular to a sagittal plane through the subject's body. FIG. 6 illustrates a subject's head at three different angles with respect to the horizontal plane 20, with $\beta=-30°$, $\beta=0°$ and $\beta=30°$. When $\beta=0°$ the subject's head is referred to as being 'upright', and in this illustration, negative angles represent the subject's head tilting forward from the upright position and positive angles represent the subject's head tilting backwards from the upright position. The angle $\beta$ can be used to calculate the ICP in a similar way to the angle $\alpha$ in equations (3)(6) above. The angle $\alpha_0$ that is used to determine the initial height difference between the intraocular space and the intracranial space when the head is in an upright position in FIG. 2 is also used when the head orientation is measured as shown in FIG. 6.

It will be appreciated from the method provided above that the range of ICP that can be detected is limited by the maximum height difference possible between the intracranial space and the intraocular space in the subject (for example the height change from where the intracranial space is directly below the intraocular space to when the intracranial space is directly above the intraocular space. If the ICP differs from the IOP by more than can be compensated by changing the angle of the head (and that includes when the ICP is above or below the IOP), then changing the angle of the head will not result in the IOP equaling the ICP at any angle, which will mean that there will not be any angle where there is an onset or cessation of SRVPs in the subjects eye. Thus, when the ICP is greater than the IOP by a pressure greater than can be compensated by tilting the head, SRVPs cannot be detected, at any tilt angle. Likewise, when the ICP is less than the IOP by a pressure greater than can be compensated by tilting the head, SRVPs will be detected at all tilt angles. In this case, the method described above will not be able to provide a value for the ICP. However, where no onset or cessation of SRVPs is detected after evaluating the possible tilt angles of the head (which can be determined by assessing the range of angles measured by the orientation sensor 6), the method can instead provide an output indicating that ICP is beyond a certain threshold value. For example, if SRVPs are not present at any angle, then it can be indicated that ICP exceeds IOP+K(1−sin($\alpha_0$)), and if SRVPs are present at all angles, then it can be indicated that ICP is below IOP−K(1+sin($\alpha_0$)). Although not as useful as a measurement of the ICP itself, this information is still useful. In particular, an indication from the method that the ICP is greater than the IOP by a certain amount can provide a healthcare professional with an indication that the ICP is elevated, and thus the healthcare professional can decide whether to use a more intrusive traditional method for determining ICP. Thus, in some embodiments, the device and method described above can be used in patient stratification for additional, more obtrusive methods to measure ICP (i.e. only perform an obtrusive ICP measurement if ICP is significantly beyond a certain level).

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for measuring the intracranial pressure (ICP) in a subject, the method comprising:
   with a first sensor, detecting whether spontaneous retinal venous pulsations (SRVPs) are occurring in an eye of the subject as the orientation of the head of the subject changes;
   with a second sensor attached to a table, bed or chair on which the subject is sitting or lying, measuring the orientation of the head of the subject at which SRVPs start to occur and stop occurring, the measured orientation of the head of the subject being an angle of rotation of the head about an axis that is perpendicular to a sagittal plane through the head or body of the subject; and
   with a control unit, using the measured orientation of the head of the subject at which SRVPs start to occur or stop occurring to determine the ICP in the subject by determining a pressure difference between an intraocular pressure (IOP) in the eye of the subject and the ICP at a predetermined orientation using the measured orientation.

2. The method as claimed in claim 1, wherein using the measured orientation to determine the ICP in the subject further comprises:
   determining the ICP from a measurement of the TOP in the eye of the subject at the predetermined orientation and the determined pressure difference at the predetermined orientation.

3. The method as claimed in claim 2, wherein, in the event that no orientation is identified at which SRVPs start to occur or stop occurring, the method further comprises:
   providing an output indicating that the ICP is beyond a threshold value.

4. The method as claimed in claim 1, wherein the method further comprises:
   changing the orientation of the table, bed or chair to change the orientation of the head of the subject while detecting, with the first sensor, whether SRVPs are occurring in the eye of the subject.

5. The method as claimed in claim 1, wherein the second sensor is one of an accelerometer, a gyroscope or a camera, and the first sensor is a pulse oximeter.

6. A non-transitory computer readable medium having computer readable code embodied therein, the computer readable code being configured such that, on execution by a suitable computer, processor or control unit, the computer, processor or control unit is caused to perform the method of claim 1.

7. A device for measuring the intracranial pressure (ICP) in a subject, the device comprising:
   a first sensor configured to detect whether spontaneous retinal venous pulsations (SRVPs) are occurring in the eye of the subject as the orientation of the head of the subject changes;
   a second sensor configured to measure an angle of rotation of the head about an axis that is perpendicular to a sagittal plane through the head or body of the subject; and
   a control unit configured to:
   identify the orientation of the head of the subject at which SRVPs start to occur and stop occurring from outputs from the first sensor and second sensor; and
   use the measured orientation of the head of the subject at which SRVPs start to occur and stop occurring to determine the ICP in the subject by determining a pressure difference between the intraocular pressure (TOP) in the eye of the subject and the ICP at a predetermined orientation using the measured orientation.

8. The device as claimed in claim 7, wherein the control unit is configured to use the identified orientation to determine the ICP in the subject by determining the ICP from a measurement of the IOP in the eye of the subject at the predetermined orientation and the determined pressure difference at the predetermined orientation.

9. The device as claimed in claim 8, wherein the device further comprises a sensor or measuring apparatus for measuring the TOP of the subject.

10. The device as claimed in claim 9, wherein the device is configured to be worn on the head of the subject.

11. The device as claimed in claim 9, wherein the second sensor is attached to or otherwise part of a table, bed or chair on which the subject is to sit or lie, wherein the table, bed or chair is adapted so that the orientation of the table, bed or chair can be changed in order to change the orientation of the head of the subject.

12. The device as claimed in claim 11, wherein the second sensor is an accelerometer, a gyroscope or a camera, and the first sensor is a pulse oximeter.

13. The device as claimed in claim 7, wherein, in the event that no orientation is identified at which SRVPs start to occur or stop occurring, the method further comprises:
   providing an output indicating that the ICP is beyond a threshold value.

14. A device for measuring the intracranial pressure (ICP) in a subject, the device comprising:
   a sensor configured to measure an intraocular pressure (IOP) in the eye of the subject;
   a pulse oximeter configured to detect whether spontaneous retinal venous pulsations (SRVPs) are occurring in the eye of the subject as the orientation of the head of the subject changes;
   a camera configured to measure an angle of rotation of the head about an axis that is perpendicular to a sagittal plane through the head or body of the subject; and
   at least one processor programmed to:
   identify an orientation of the head of the subject at which SRVPs start to occur or stop occurring from outputs from the first sensor and second sensor; and
   determine the ICP in the subject from the measured angle of rotation by determining a pressure difference between a measurement of an intraocular pressure (IOP) in the eye of the subject and the ICP at a predetermined orientation using the identified orientation; and determine the ICP in the subject by determining the ICP from in the eye of the subject at the predetermined orientation and the determined pressure difference at the predetermined orientation.

15. The device as claimed in claim 14, wherein, in the event that no orientation is identified at which SRVPs start to occur or stop occurring, the at least one processor is further programmed to:

providing an output indicating that the ICP is beyond a threshold value.

* * * * *